(12) United States Patent
Kawamura (10) Patent No.: US 10,806,425 B1
(45) Date of Patent: Oct. 20, 2020

(54) X-RAY IMAGING APPARATUS (71) Applicant: SHIMADZU CORPORATION, Kyoto (JP)

(72) Inventor: Takahiro Kawamura, Kyoto (JP)

(73) Assignee: Shimadzu Corporation, Kyoto (JP)

(*) Notice: Subject to any disclaimer, the term of this patent is extended or adjusted under 35 U.S.C. 154(b) by 0 days.

(21) Appl. No.: 16/563,291

(22) Filed: Sep. 6, 2019

(30) Foreign Application Priority Data

Apr. 10, 2019 (JP) .................. 2019-075109

(51) Int. Cl.
*A61B 5/00* (2006.01)
*A61B 6/00* (2006.01)
*A61B 6/04* (2006.01)

(52) U.S. Cl.
CPC .............. *A61B 6/54* (2013.01); *A61B 6/0407* (2013.01); *A61B 6/46* (2013.01)

(58) Field of Classification Search
CPC .......... A61B 1/00039; A61B 1/000147; A61B 5/704; A61B 6/03; A61B 6/0407; A61B 6/54; A61B 6/56; A61B 8/54; A61B 2017/00199; A61B 34/25; A61B 34/10; A61B 2562/247; G06N 3/0454
See application file for complete search history.

(56) References Cited

U.S. PATENT DOCUMENTS

2014/0039351 A1* 2/2014 Mix ..................... A61B 5/6892
600/587

FOREIGN PATENT DOCUMENTS

JP 2011-224120 11/2011

* cited by examiner

*Primary Examiner* — Don K Wong
(74) *Attorney, Agent, or Firm* — Andrew F. Young, Esq.; Lackenbach Siegel, LLP (57) ABSTRACT

An X-ray imaging apparatus includes an operation panel including a plurality of operation input units and disposed on an X-ray imaging table, and a substrate including circuits disposed inside the operation panel and configured to output signals due to operation of the plurality of operation input units and a sensor configured to sense ingress of liquid.

9 Claims, 6 Drawing Sheets

X-RAY IMAGING APPARATUS

CROSS-REFERENCE TO RELATED APPLICATIONS

This application claims the benefit of priority to Japanese Patent Application No. 2019-075109 filed on Apr. 10, 2019. The entire contents of this application are hereby incorporated herein by reference.

BACKGROUND OF THE INVENTION

Field of the Invention

The present invention relates to an X-ray imaging apparatus.

Description of the Background Art

Conventionally, an X-ray fluoroscopic imaging apparatus including an operation panel is known. Such an X-ray fluoroscopic imaging apparatus is disclosed in Japanese Patent Laid-Open No. 2011-224120, for example.

Japanese Patent Laid-Open No. 2011-224120 discloses an X-ray fluoroscopic imaging apparatus including an examination table including a top board on which a subject is placed, an X-ray tube that irradiates the subject placed on the top board with X-rays, and an X-ray detector that faces the X-ray tube with the subject interposed between the X-ray detector and the X-ray tube and detects the X-rays transmitted through the subject.

The X-ray fluoroscopic imaging apparatus disclosed in Japanese Patent Laid-Open No. 2011-224120 further includes an operation panel provided at the outer edge of the examination table and through which an operation is input.

Although not disclosed in Japanese Patent Laid-Open No. 2011-224120, during fluoroscopic imaging using an X-ray fluoroscopic imaging apparatus (X-ray imaging apparatus), administration of a drug to a subject or collection of a specimen, such as blood, from a subject may be performed. In this case, liquid such as a drug and a specimen may spill on the examination table. In addition, when the X-ray fluoroscopic imaging apparatus (X-ray imaging apparatus) is wiped and cleaned with a cloth or the like, liquid such as water contained in the cloth or the like may also spill on the examination table. In such a case, the liquid may enter the X-ray imaging apparatus from the operation panel provided at the outer edge of the examination table, and the entered liquid may contact a substrate electrically connected to the operation panel and disposed inside the X-ray imaging apparatus.

Therefore, in consideration of the above possibility, when the liquid enters the substrate electrically connected to the operation panel of an X-ray imaging apparatus main body and disposed inside the X-ray imaging apparatus, it is desired to develop an X-ray imaging apparatus capable of sensing the ingress of liquid.

SUMMARY OF THE INVENTION

The present invention has been proposed in order to solve the aforementioned problems, and an object of the present invention is to provide an X-ray imaging apparatus capable of sensing the ingress of liquid into a substrate electrically connected to an operation panel of an X-ray imaging apparatus main body and disposed inside the operation panel.

In order to attain the aforementioned object, an X-ray imaging apparatus according to as aspect of the present invention includes an X-ray imaging table including a top board on which a subject is placed, an imager including an X-ray source configured to irradiate the subject with X-rays, and an X-ray detector configured to detect the X-rays emitted from the X-ray source and transmitted through the subject, an operation panel including a plurality of operation input units and disposed on the X-ray imaging table, and a substrate including circuits disposed inside the operation panel and configured to output signals due to operation of the plurality of operation input units, and a sensor configured to sense ingress of liquid.

As described above, the X-ray imaging apparatus according to this aspect of the present invention includes the operation panel including the plurality of operation input units and disposed on the X-ray imaging table, and the substrate including the circuits disposed inside the operation panel and configured to output the signals due to operation of the operation input units and the sensor configured to sense the ingress of the liquid. Accordingly, the sensor is provided in the substrate including the circuits connected to the operation panel such that it is possible to sense the ingress of the liquid into the substrate electrically connected to the operation panel of a main body of the X-ray imaging apparatus and disposed inside the X-ray imaging apparatus.

In the aforementioned X-ray imaging apparatus according to this aspect, the sensor preferably includes a first conductive pattern disposed on a surface of the substrate and a second conductive pattern spaced apart from the first conductive pattern on the surface of the substrate, and is preferably configured to sense the ingress of the liquid based on a short circuit between the first conductive pattern and the second conductive pattern. According to this structure, the first conductive pattern and the second conductive pattern are spaced apart from each other such that the short circuit between the first conductive pattern and the second conductive pattern does not occur when the liquid does not enter the substrate. When the entered liquid comes into contact with the first conductive pattern and the second conductive pattern, the first conductive pattern and the second conductive pattern are short-circuited. Therefore, it is possible to sense the ingress of the liquid by sensing the short circuit between the first conductive pattern and the second conductive pattern.

In this case, the first conductive pattern and the second conductive pattern are preferably disposed side by side at a predetermined interval in such a manner as to surround the circuits. According to this structure, the first conductive pattern and the second conductive pattern are disposed in such a manner as to surround the circuits such that when the liquid enters the substrate from its outer periphery, the ingress of the liquid can be reliably sensed before the liquid reaches the circuits. In addition, the manufacturing cost of the operation panel can be reduced as compared with the case in which the sensor configured to sense the ingress of the liquid is provided for each of the plurality of operation input units in the operation panel.

In the structure in which the sensor includes the first conductive pattern disposed on the surface of the substrate and the second conductive pattern spaced apart from the first conductive pattern on the surface of the substrate, the sensor preferably further includes a power supply, a resistor, and a sensing circuit, all of which are connected to the first conductive pattern, and the second conductive pattern is preferably connected to a ground. According to this structure, when the first conductive pattern and the second conductive pattern are not short-circuited, the voltage of the power supply is transmitted to the sensing circuit. On the other hand, when the first conductive pattern and the second conductive pattern are short-circuited, the power supply is connected to the ground. In this case, the voltage sensed by the sensing circuit is smaller than in the case in which no short circuit occurs. Thus, the sensor can sense the short circuit between the first conductive pattern and the second conductive pattern with the sensing circuit, using the voltage difference. Consequently, it is possible to easily sense the ingress of the liquid with a simple structure that only monitors the level of the voltage input into the sensing circuit.

In this case, the second conductive pattern is preferably disposed outside the first conductive pattern. According to this structure, the sensing circuit and the first conductive pattern to which the sensing circuit is connected can be disposed inside the second conductive pattern. Therefore, it is not necessary to dispose the wiring, which connects the sensing circuit to the first conductive pattern, across the second conductive pattern, and thus the sensing circuit and the first conductive pattern can be easily connected to each other by the wiring.

In the aforementioned X-ray imaging apparatus according to this aspect, the first conductive pattern and the second conductive pattern are preferably disposed along an outer periphery of the surface of the substrate. According to this structure, the first conductive pattern and the second conductive pattern are disposed along the outer periphery of the surface of the substrate such that when there are a plurality of circuits corresponding to a plurality of operation input units, the first conductive pattern and the second conductive pattern can be disposed in such a manner as to surround all the plurality of circuits. Consequently, as compared with the case in which the first conductive pattern and the second conductive pattern are disposed for each circuit, the structure of the first conductive pattern and the structure of the second conductive pattern can be simplified.

In the aforementioned X-ray imaging apparatus according to this aspect, the first conductive pattern and the second conductive pattern are preferably provided on both a front surface and a back surface of the substrate. According to this structure, the sensor can sense the ingress of the liquid regardless of whether the liquid enters the front surface or the back surface of the substrate.

The aforementioned X-ray imaging apparatus according to this aspect preferably further includes a controller configured or programmed to perform control not to process the signals output from the circuits when the first conductive pattern and the second conductive pattern are short-circuited. According to this structure, even when the liquid enters the substrate and the output signals not based on user operation are output from the circuits, the controller does not process the output signals such that the operation of the X-ray imaging apparatus not intended by the user can be significantly reduced or prevented.

The aforementioned X-ray imaging apparatus according to this aspect preferably further includes a display configured to display a warning when the first conductive pattern and the second conductive pattern are short-circuited. According to this structure, by the warning displayed on the display, the user recognizes that the liquid has entered the substrate disposed inside the X-ray imaging apparatus and electrically connected to the operation panel. Therefore, continuous use of the X-ray imaging apparatus without being aware of the ingress of the liquid can be significantly reduced or prevented, and the ingress of the liquid can be promptly dealt with.

The foregoing and other objects, features, aspects and advantages of the present invention will become more apparent from the following detailed description of the present invention when taken in conjunction with the accompanying drawings.

DESCRIPTION OF THE PREFERRED EMBODIMENTS

An embodiment of the present invention is hereinafter described with reference to the drawings.

This Embodiment

The structure of an X-ray imaging apparatus 100 according to the embodiment is now described with reference to FIGS. 1 to 5.

(Structure of X-ray Imaging Apparatus)

Figure 1:
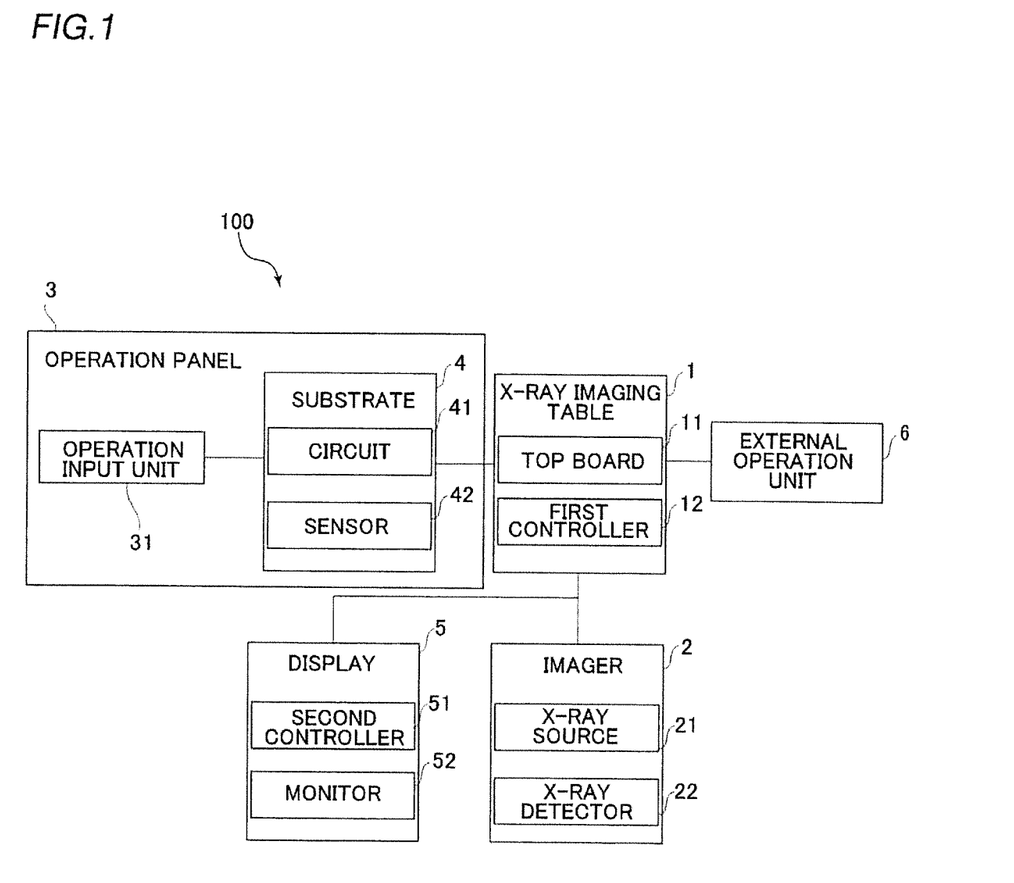
FIG. 1 is a block diagram showing the overall structure of an X-ray imaging apparatus.

As shown in FIG. 1, the X-ray imaging apparatus 100 according to this embodiment includes an X-ray imaging table 1, an imager 2, an operation panel 3, and a substrate 4. The X-ray imaging apparatus 100 further includes a display 5 and an external operation unit 6.

Figure 2:
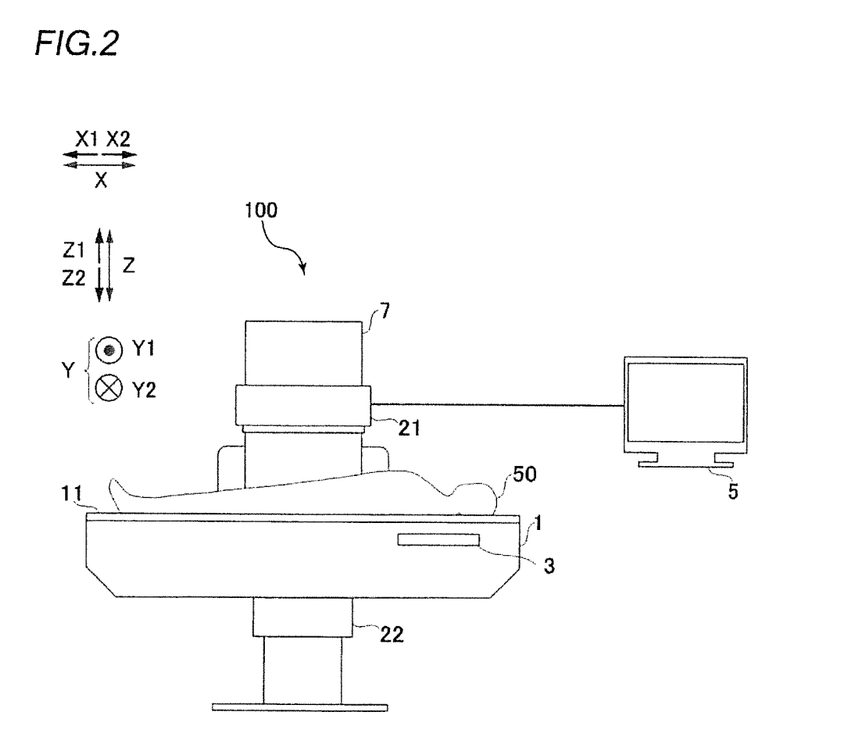
FIG. 2 is a schematic view showing an example of the X-ray imaging apparatus.

As shown in FIGS. 1 and 2, the X-ray imaging table 1 includes a top board 11. A subject 50 is placed on the top board 11. The top board 11 has a rectangular flat plate shape in a plan view. The subject 50 is placed on the top board in such a manner that the head-foot direction of the subject 50 is along the long side of the rectangular shape and the right-left direction of the subject 50 is along the short side of the rectangular shape. The head-foot direction of the subject 50 is a direction along a straight line that connects the head and the foot of the subject 50 to each other.

The X-ray imaging table 1 is supported by a support 7. A user operates the operation panel 3 such that the X-ray imaging table 1 is moved in X and Y directions with the support 7 as an axis. Moreover, the user operates the operation panel 3 such that the angle of the X-ray imaging table 1 with respect to the support 7 can be changed.

As shown in FIG. 1, the X-ray imaging table 1 further includes a first controller 12. Output signals output from operation input units 31 of the operation panel 3 are processed by the first controller 12. The first controller 12 is an example of a "controller" in the claims.

The imager 2 includes an X-ray source 21 and an X-ray detector 22. The imager 2 is configured to capture an X-ray image by detecting X-rays emitted from the X-ray source 21 to the subject 50 with the X-ray detector 22. The X-ray source 21 is configured to irradiate the subject 50 with X-rays due to a voltage applied by an X-ray tube drive (not shown).

The X-ray detector 22 is configured to detect the X-rays emitted from the X-ray source 21 and transmitted through the subject 50. The X-ray detector 22 includes a flat panel detector (FPD), for example. The X-ray detector 22 includes a plurality of conversion elements (not shown) and pixel electrodes (not shown) disposed on the plurality of conversion elements. The plurality of conversion elements and the pixel electrodes are arranged in an array on a detection surface at a predetermined cycle (pixel pitch).

Figure 3:
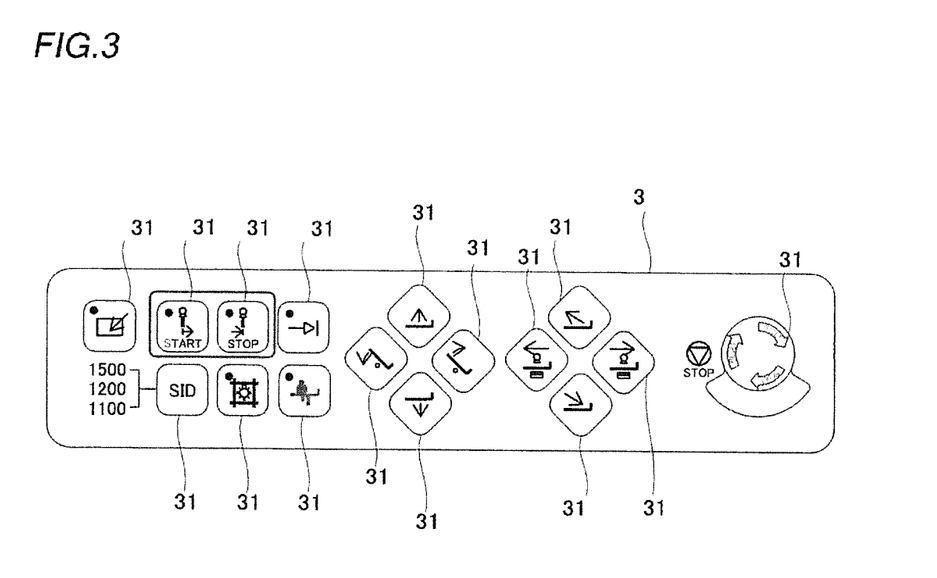
FIG. 3 is a diagram showing an example of an operation panel.

As shown in FIGS. 2 and 3, the operation panel 3 is provided on the X-ray imaging table 1. The operation panel 3 includes a plurality of operation input units 31. The operation input units 31 are configured in the form of a single sheet. The operation input units 31 include position adjustment buttons for the X-ray imaging table 1 and operation authority buttons, for example.

The position adjustment buttons for the X-ray imaging table 1 include buttons for moving the top board 11 in the X and Y directions with the support 7 as an axis. Furthermore, the position adjustment buttons for the X-ray imaging table 1 are used to change the angle of the top board 11 with respect to the support 7 and to tilt the top board 11.

The operation authority buttons are buttons for determining the operation authority of the X-ray imaging apparatus 100. The X-ray imaging apparatus 100 operates due to an input signal from one having the operation authority among the operation panel 3 provided on the X-ray imaging table 1 and the external operation unit 6 (see FIG. 1) through which the X-ray imaging apparatus 100 is operated from a distant place. The operation authority buttons are used to switch the operation authority between the operation panel 3 and the external operation unit 6.

Figure 4:
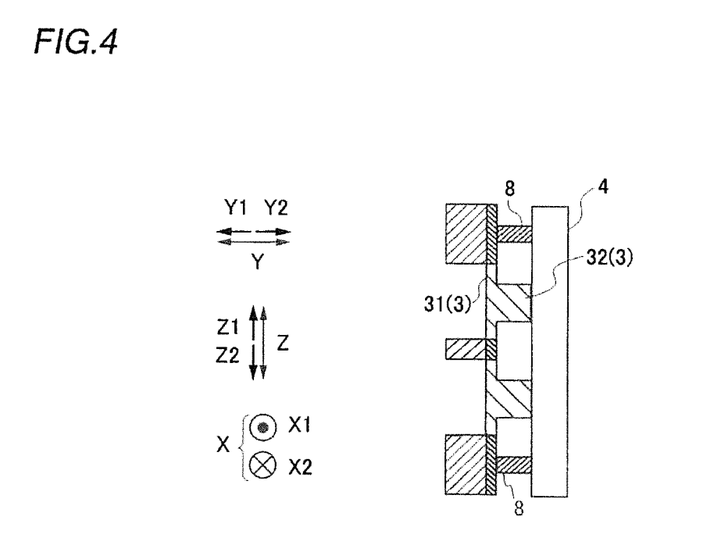
FIG. 4 is a schematic view showing the inside of the operation panel.

The operation panel 3 is fixed to the X-ray imaging table 1 by screws, for example, and can be removed. Furthermore, the operation panel 3 is removed such that the substrate 4 disposed inside the operation panel 3 can be replaced. As shown in FIG. 4, spacers 8 are disposed between the operation input units 31 and the substrate 4. The Y1 direction side in FIG. 4 is the front side of the operation input units 31. The spacers 8 are provided such that switches 32 are activated by operating the operation input units 31. The switches 32 are activated and electrically connected to circuits 41 of the substrate 4 such that on signals are output to the first controller 12.

Figure 5:
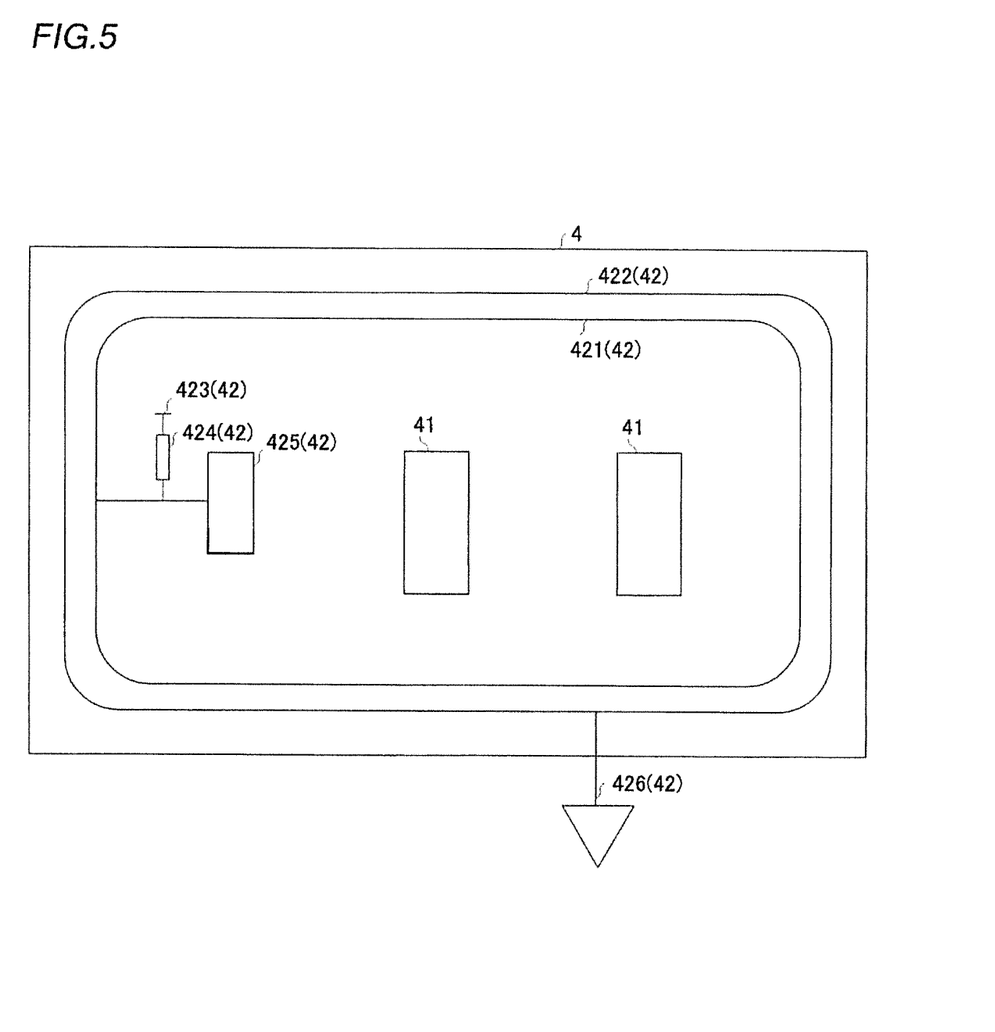
FIG. 5 is a diagram showing an example of an arrangement of a first conductive pattern and a second conductive pattern.

FIG. 5 is a diagram schematically showing the substrate 4 provided inside the operation panel 3 shown in FIG. 3. The substrate 4 includes a plurality of circuits 41 corresponding to the plurality of operation input units 31 and a sensor 42. The plurality of circuits 41 are provided corresponding to the plurality of operation input units 31. The user operates each of the operation input units 31 such that the corresponding circuit 41 is switched on or off. Then, an on signal or an off signal is output from the substrate 4 to the first controller 12. When receiving the on signal, the first controller 12 performs control according to the signal. When receiving the off signal in an on-state, the first controller 12 stops the operation of the X-ray imaging apparatus 100 according to the off signal. Although two circuits 41 are schematically illustrated in FIG. 5, the number of circuits 41 is not limited to two.

As shown in FIG. 5, the sensor 42 includes a first conductive pattern 421, a second conductive pattern 422, a power supply 423, a resistor 424, a sensing circuit 425, and a ground 426. The first conductive pattern 421 and the second conductive pattern 422 are provided on both the front surface and the back surface of the substrate 4. The first conductive pattern 421 and the second conductive pattern 422 are metal wires having high conductivity, for example. The first conductive pattern 421 and the second conductive pattern 422 are concentrically disposed side by side in such a manner as to surround the plurality of circuits 41. Furthermore, a predetermined interval is provided between the first conductive pattern 421 and the second conductive pattern 422. The predetermined interval is an interval at which entered liquid can contact the first conductive pattern 421 and the second conductive pattern 422. For example, when the substrate 4 has a size of 10 mm×20 mm, the predetermined interval is about 1 mm.

The second conductive pattern 422 is provided closer to the outer peripheral side of the substrate 4 as compared with the first conductive pattern 421. In addition, the first conductive pattern 421 and the second conductive pattern 422 are annularly disposed along the outer periphery of the surface of the substrate 4. The first conductive pattern 421 is connected to the sensing circuit 425. The power supply 423 and the resistor 424 are connected between the first conductive pattern 421 and the sensing circuit 425. The second conductive pattern 422 is connected to the ground 426. The sensing circuit 425 is an integrated circuit (IC), for example.

The power supply 423 is a VCC power supply, for example. The resistor 424 is a pull-up resistor, for example. The first conductive pattern 421 and the second conductive pattern 422 are electrically insulated from each other. When there is no short circuit between the first conductive pattern 421 and the second conductive pattern 422, a voltage is transmitted from the power supply 423 to the sensing circuit 425 such that the input voltage of the sensing circuit 425 is substantially equal to the voltage of the power supply 423, and thus the sensing circuit 425 senses the potential in a high state (H-level). When the liquid contacts the first conductive pattern 421 and the second conductive pattern 422 and the first conductive pattern 421 and the second conductive pattern 422 are short-circuited, the first conductive pattern 421 and the second conductive pattern 422 is electrically connected to each other. At this time, the input voltage of the sensing circuit 425 decreases as the first conductive pattern 421 and the second conductive pattern 422 are connected to each other. The resistance value of the resistor 424 is sufficiently increased such that the input voltage of the sensing circuit 425 at the time of short circuit substantially matches the ground potential. Then, the voltage is transmitted to the ground 426 via the second conductive pattern 422. Then, the voltage is transmitted to the second conductive pattern 422, and thus the amount of voltage transmitted to the sensing circuit 425 is smaller than before the short circuit. Consequently, the sensing circuit 425 senses the potential in a low state (L-level), and outputs a sensing signal to the first controller 12. A doctor may treat or examine the subject 50 while the X-ray imaging apparatus 100 performs fluoroscopic imaging. Therefore, examples of the liquid are a drug such as a contrast agent used for treatment, and a specimen such as the blood or urine of the subject 50 collected from the subject 50 for examination.

As shown in FIG. 1, the display 5 includes a second controller 51 and a monitor 52. The second controller 51 controls the monitor 52 to display the acquired X-ray image acquired by the imager 2. The second controller 51 controls the monitor 52 to display a warning based on the sensing signal from the first controller 12. The second controller 51 is an example of a "controller" in the claims. The monitor 52 displays an X-ray image as a moving image. Therefore, the user can treat or examine the subject 50 while checking the X-ray image.

The external operation unit 6 is a console, for example. The user operates the X-ray imaging apparatus 100 via the external operation unit 6.

Figure 6:
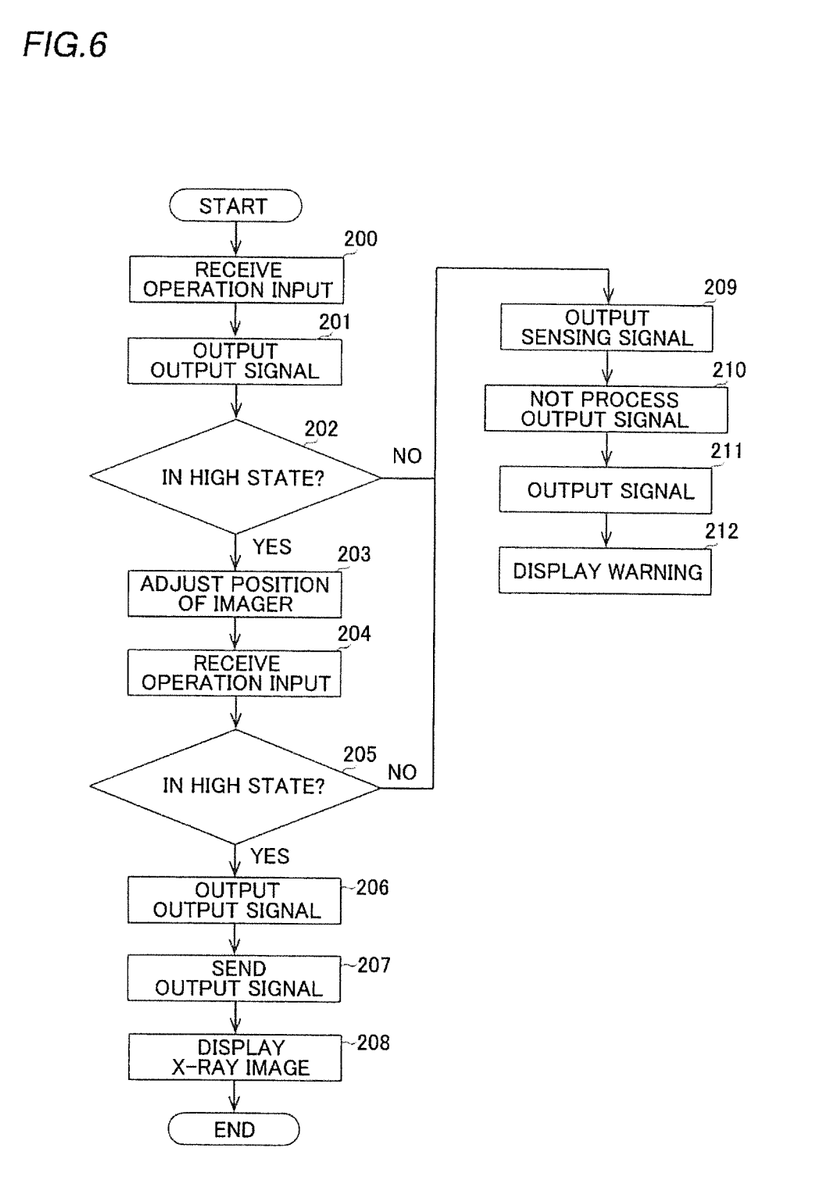
FIG. 6 is a diagram showing an example of the operation of the X-ray imaging apparatus.

The operation of the X-ray imaging apparatus 100 according to this embodiment is now described with reference to FIG. 6.

In step 200, the substrate 4 receives an operation input for adjusting the positions of the subject 50 and the imager 2. A technologist who performs radiation imaging inputs the operation, for example.

In step 201, in the substrate 4, the circuit 41 for the operated operation input unit 31 is switched from an off-state to an on-state. Then, the substrate 4 outputs an output signal in the on-state to the first controller 12.

In step 202, the sensing circuit 425 senses whether or not the potential of the first conductive pattern 421 is in the high state. When the potential is in the high state, the processing advances to step 203, and when the potential is not in the high state (is in the low state), the processing advances to step 209.

In step 203, the first controller 12 performs control of adjusting the positions of the subject 50 and the imager 2 based on the output signal.

In step 204, the substrate 4 receives an operation input for starting X-ray imaging via the operation input unit 31. The technologist who performs radiation inputs the operation, for example.

In step 205, the sensing circuit 425 senses whether or not the potential of the first conductive pattern 421 is in the high state. When the potential is in the high state, the processing advances to step 206, and when the potential is not in the high state (is in the low state), the processing advances to step 209.

In step 206, the circuit 41 for the operated operation input unit 31 is switched from the off-state to the on-state, and thus the substrate 4 outputs an output signal in the on-state to the first controller 12.

In step 207, the first controller 12 communicates with the imager 2 and sends an output signal. The imager 2 that has received the signal starts X-ray imaging.

In step 208, the second controller 51 controls the monitor 52 to display an X-ray image. Then, while viewing the X-ray image displayed on the monitor 52, the doctor starts treatment or examination. For example, the doctor performs treatment using a catheter while checking the x-ray image. In addition, the doctor uses the catheter to collect a specimen while checking the X-ray image.

The case in which the sensing circuit 425 senses that the potential of the first conductive pattern 421 is not in the high state (is in the low state) is now described. In step 209, when the sensing circuit 425 senses the low state of the first conductive pattern 421, the sensing circuit 425 outputs a sensing signal to the first controller 12.

In step 210, the first controller 12 performs control not to process the output signal output from the substrate 4 based on the sensing signal received from the sensing circuit 425.

In step 211, the first controller 12 communicates with the second controller 51 and sends a signal so as to control the monitor 52 to display a warning.

In step 212, the second controller 51 controls the monitor 52 to display the warning. The user takes measures according to the warning displayed on the monitor 52.

Advantages of This Embodiment

According to this embodiment, the following advantages are obtained.

According to this embodiment, as described above, the X-ray imaging apparatus 100 includes the operation panel 3 including the plurality of operation input units 31 and disposed on the X-ray imaging table 1, and the substrate 4 including the circuits 41 disposed inside the operation panel 3 and configured to output the output signals due to operation of the operation input units 31 and the sensor 42 configured to sense the ingress of the liquid. Accordingly, the sensor 42 is provided in the substrate 4 including the circuits 41 connected to the operation panel 3 such that it is possible to sense the ingress of the liquid into the substrate 4 electrically connected to the operation panel 3 of a main body of the X-ray imaging apparatus 100 and disposed inside the X-ray imaging apparatus 100.

According to this embodiment, as described above, the sensor 42 includes the first conductive pattern 421 disposed on the surface of the substrate 4 and the second conductive pattern 422 spaced apart from the first conductive pattern 421 on the surface of the substrate 4, and is configured to sense the ingress of the liquid based on the short circuit between the first conductive pattern 421 and the second conductive pattern 422. Accordingly, the first conductive pattern 421 and the second conductive pattern 422 are spaced apart from each other such that the short circuit between the first conductive pattern 421 and the second conductive pattern 422 does not occur when the liquid does not enter the substrate 4. When the entered liquid comes into contact with the first conductive pattern 421 and the second conductive pattern 422, the first conductive pattern 421 and the second conductive pattern 422 are short-circuited. Therefore, it is possible to sense the ingress of the liquid by sensing the short circuit between the first conductive pattern 421 and the second conductive pattern 422.

According to this embodiment, as described above, the first conductive pattern 421 and the second conductive pattern 422 are disposed side by side at the predetermined interval in such a manner as to surround the circuits 41. Accordingly, the first conductive pattern 421 and the second conductive pattern 422 are disposed in such a manner as to surround the circuits 41 such that when the liquid enters the substrate 4 from its outer periphery, the ingress of the liquid can be reliably sensed before the liquid reaches the circuits 41. In addition, the manufacturing cost of the operation panel 3 can be reduced as compared with the case in which the sensor 42 configured to sense the ingress of the liquid is provided for each of the plurality of operation input units 31 in the operation panel 3.

According to this embodiment, as described above, the sensor 42 further includes the power supply 423, the resistor 424, and the sensing circuit 425, all of which are connected to the first conductive pattern 421, and the second conductive pattern 422 is connected to the ground 426. Accordingly, when the first conductive pattern 421 and the second conductive pattern 422 are not short-circuited, the voltage of the power supply 423 is transmitted to the sensing circuit 425. On the other hand, when the first conductive pattern 421 and the second conductive pattern 422 are short-circuited, the power supply 423 is connected to the ground 426. In this case, the voltage sensed by the sensing circuit 425 is smaller than in the case in which no short circuit occurs. Thus, the sensor 42 can sense the short circuit between the first conductive pattern 421 and the second conductive pattern 422 with the sensing circuit 425, using the voltage difference. Consequently, it is possible to easily sense the ingress of the liquid with a simple structure that only monitors the level of the voltage input into the sensing circuit 425.

According to this embodiment, as described above, the second conductive pattern 422 is disposed outside the first conductive pattern 421. Accordingly, the sensing circuit 425 and the first conductive pattern 421 to which the sensing circuit 425 is connected can be disposed inside the second conductive pattern 422. Therefore, it is not necessary to dispose the wiring, which connects the sensing circuit 425 to the first conductive pattern 421, across the second conductive pattern 422, and thus the sensing circuit 425 and the first conductive pattern 421 can be easily connected to each other by the wiring.

According to this embodiment, as described above, the first conductive pattern 421 and the second conductive pattern 422 are disposed along the outer periphery of the surface of the substrate 4. Accordingly, the first conductive pattern 421 and the second conductive pattern 422 are disposed along the outer periphery of the surface of the substrate 4 such that when there are a plurality of circuits 41 corresponding to a plurality of operation input units 31, the first conductive pattern 421 and the second conductive pattern 422 can be disposed in such a manner as to surround all the plurality of circuits 41. Consequently, as compared with the case in which the first conductive pattern 421 and the second conductive pattern 422 are disposed for each circuit 41, the structure of the first conductive pattern 421 and the structure of the second conductive pattern 422 can be simplified.

According to this embodiment, as described above, the first conductive pattern 421 and the second conductive pattern 422 are provided on both the front surface and the back surface of the substrate 4. Accordingly, the sensor 42 can sense the ingress of the liquid regardless of whether the liquid enters the front surface or the back surface of the substrate 4.

According to this embodiment, as described above, the X-ray imaging apparatus 100 further includes the first controller 12 configured or programmed to perform control not to process the output signals from the circuits 41 when the first conductive pattern 421 and the second conductive pattern 422 are short-circuited. Accordingly, even when the liquid enters the substrate 4 and the output signals not based on user operation are output from the circuits 41, the first controller 12 does not process the output signals such that the operation of the X-ray imaging apparatus 100 not intended by the user can be significantly reduced or prevented.

According to this embodiment, as described above, the X-ray imaging apparatus 100 further includes the display 5 configured to display a warning when the first conductive pattern 421 and the second conductive pattern 422 are short-circuited. Accordingly, by the warning displayed on the display 5, the user recognizes that the liquid has entered the substrate 4 disposed inside the X-ray imaging apparatus 100 and electrically connected to the operation panel 3. Therefore, continuous use of the X-ray imaging apparatus without being aware of the ingress of the liquid can be significantly reduced or prevented, and the ingress of the liquid can be promptly dealt with.

Modified Examples

The embodiment disclosed this time must be considered as illustrative in all points and not restrictive. The scope of the present invention is not shown by the above description of the embodiment but by the scope of claims for patent, and all modifications (modified examples) within the meaning and scope equivalent to the scope of claims for patent are further included.

For example, while the monitor displays an X-ray image as a moving image in the aforementioned embodiment, the present invention is not limited to this. The monitor may alternatively display an X-ray image as a still image.

While the first conductive pattern and the second conductive pattern are disposed along the outer periphery of the surface of the substrate in such a manner as to surround all the plurality of circuits in the aforementioned embodiment, the present invention is not limited to this. The first conductive pattern and the second conductive pattern may alternatively be disposed for each of the plurality of circuits.

While the second conductive pattern is disposed outside the first conductive pattern in the aforementioned embodiment, the present invention is not limited to this. The second conductive pattern may alternatively be disposed inside the first conductive pattern.

While the first conductive pattern and the second conductive pattern are provided on both the front surface and the back surface of the substrate in the aforementioned embodiment, the present invention is not limited to this. The first conductive pattern and the second conductive pattern may alternatively be provided on one of the front surface and the back surface of the substrate.

While the sensing circuit senses the potential when the first conductive pattern and the second conductive pattern are short-circuited in the aforementioned embodiment, the present invention is not limited to this. The sensing circuit may alternatively sense the current when the first conductive pattern and the second conductive pattern are short-circuited.

While the sensing circuit is switched from the high state (H-level) to the low state (L-level) when the first conductive pattern and the second conductive pattern are short-circuited in the aforementioned embodiment, the present invention is not limited to this. The sensing circuit may alternatively be switched from the low state to the high state when the first conductive pattern and the second conductive pattern are short-circuited. That is, in the sensor, an L-level potential may be input into the sensing circuit when no short circuit occurs, and an H-level potential may be input into the sensing circuit when a short circuit occurs.

What is claimed is:

1. An X-ray imaging apparatus, comprising:
    an X-ray imaging table including a top board on which a subject is placed;
    an imager including an X-ray source configured to irradiate the subject with X-rays, and an X-ray detector configured to detect the X-rays emitted from the X-ray source and transmitted through the subject;
    an operation panel including a plurality of operation input units and disposed on the X-ray imaging table; and
    a substrate including circuits disposed inside the operation panel and configured to output signals due to operation of the plurality of operation input units, and a sensor configured to sense ingress of liquid.

2. The X-ray imaging apparatus according to claim 1, wherein:
    the sensor includes a first conductive pattern disposed on a surface of the substrate and a second conductive pattern spaced apart from the first conductive pattern on the surface of the substrate, and is configured to sense the ingress of the liquid based on a short circuit between the first conductive pattern and the second conductive pattern.

3. The X-ray imaging apparatus according to claim 2, wherein:
the first conductive pattern and the second conductive pattern are disposed side by side at a predetermined interval in such a manner as to surround the circuits.

4. The X-ray imaging apparatus according to claim 2, wherein:
the sensor further includes a power supply, a resistor, and a sensing circuit, all of which are connected to the first conductive pattern; and
the second conductive pattern is connected to a ground.

5. The X-ray imaging apparatus according to claim 4, wherein:
the second conductive pattern is disposed outside the first conductive pattern.

6. The X-ray imaging apparatus according to claim 2, wherein:
the first conductive pattern and the second conductive pattern are disposed along an outer periphery of the surface of the substrate.

7. The X-ray imaging apparatus according to claim 2, wherein:
the first conductive pattern and the second conductive pattern are provided on both a front surface and a back surface of the substrate.

8. The X-ray imaging apparatus according to claim 2, further comprising:
a controller configured or programmed to perform control not to process the signals output from the circuits when the first conductive pattern and the second conductive pattern are short-circuited.

9. The X-ray imaging apparatus according to claim 2, further comprising:
a display configured to display a warning when the first conductive pattern and the second conductive pattern are short-circuited.

\* \* \* \* \*